United States Patent
Mojarrad et al.

(10) Patent No.: US 12,070,582 B2
(45) Date of Patent: Aug. 27, 2024

(54) DRUG DELIVERY SYSTEM WITH FLEXIBLE PISTON ASSEMBLY

(71) Applicant: AMGEN INC., Thousand Oaks, CA (US)

(72) Inventors: Mehran Mojarrad, Thousand Oaks, CA (US); Ali Nekouzadeh, Simi Valley, CA (US); Susan McConnell Montalvo, Thousand Oaks, CA (US); Scott R. Gibson, Granada Hills, CA (US); Sheldon B. Moberg, Thousand Oaks, CA (US); Joshua Tamsky, Los Angeles, CA (US); Paul D. Faucher, Escondido, CA (US)

(73) Assignee: AMGEN INC., Thousand Oaks, CA (US)

( * ) Notice: Subject to any disclaimer, the term of this patent is extended or adjusted under 35 U.S.C. 154(b) by 732 days.

(21) Appl. No.: 17/094,176

(22) Filed: Nov. 10, 2020

(65) Prior Publication Data
US 2021/0146055 A1    May 20, 2021

Related U.S. Application Data

(60) Provisional application No. 62/949,356, filed on Dec. 17, 2019, provisional application No. 62/937,149, filed on Nov. 18, 2019.

(51) Int. Cl.
*A61M 5/315*    (2006.01)

(52) U.S. Cl.
CPC . *A61M 5/31513* (2013.01); *A61M 2005/3152* (2013.01)

(58) Field of Classification Search
CPC ...... A61M 5/31513; A61M 2005/3152; A61M 5/31511; A61M 2005/31518; A61M 2005/14204; A61M 5/14526; A61M 5/2053; A61M 5/2046; A61M 5/155
USPC ........................................................ 604/218
See application file for complete search history.

(56) References Cited

U.S. PATENT DOCUMENTS

| | | | | |
|---|---|---|---|---|
| 4,313,439 | A | * 2/1982 | Babb | A61M 5/1454 604/246 |
| 2007/0203459 | A1 | 8/2007 | Mernoe | |
| 2009/0069784 | A1 | * 3/2009 | Estes | A61M 5/16804 604/67 |
| 2014/0035604 | A1 | * 2/2014 | Paul | A61M 5/16831 604/152 |
| 2019/0175825 | A1 | * 6/2019 | McCawley | A61M 5/2046 |
| 2019/0240417 | A1 | * 8/2019 | Hostettler | A61M 5/31511 |

FOREIGN PATENT DOCUMENTS

WO    WO-2007038091 A2    4/2007

\* cited by examiner

*Primary Examiner* — Michael J Tsai
*Assistant Examiner* — Nidah Hussain
(74) *Attorney, Agent, or Firm* — MARSHALL, GERSTEIN & BORUN LLP

(57) ABSTRACT

Drug delivery devices are configured to include a gas-driven piston assembly having a flexible pushrod, a non-linear guide include a non-linear guide pathway at least partially surrounding the flexible pushrod, a cylinder at least partially surrounding the flexible pushrod, and a piston movable within the cylinder in response to the pressurized gas entering the cylinder. Some arrangements include a roller pushrod guide system and/or a gear pushrod guide system.

9 Claims, 4 Drawing Sheets

DRUG DELIVERY SYSTEM WITH FLEXIBLE PISTON ASSEMBLY

CROSS-REFERENCE TO RELATED APPLICATIONS

Priority is claimed to U.S. Provisional Patent Application No. 62/937,149, filed Nov. 18, 2019, and U.S. Provisional Patent Application No. 62/949,356, filed Dec. 17, 2019, the entire contents of each of which are incorporated herein by reference.

FIELD OF THE DISCLOSURE

The present disclosure generally relates to a drug delivery system and, in particular, to a gas-driven drug delivery system having a flexible piston assembly.

BACKGROUND

Some drug delivery devices facilitate medical injections by expelling drugs using automated drive systems as opposed to requiring manual effort. In some devices, the drive system is gas-driven. Typical gas-driven drive systems employ in-line piston designs or direct plunger drive designs. These drive systems have certain drawbacks. In-line piston designs force drug delivery devices to have a long first dimension to accommodate both the drive piston and the primary container. Drug delivery devices having a direct plunger drive designs require a secondary pressure chamber around the drug container to reduce the risk of gas entering the drug, which adds height or thickness to the device. Further, in some drug delivery devices, such drive systems have suboptimal drug pressure control or do not sufficiently isolate the driving gas.

SUMMARY

Some aspects of the present disclosure include a gas-driven drug delivery device comprising a drug container, a plunger, a gas chamber, and a piston assembly having a non-linear guide that includes a non-linear guide pathway. The drug container has a drug outlet and is configured to contain a drug. The plunger is slidably coupled with the drug container. The gas chamber is configured to contain a pressurized gas. In addition to the non-linear guide, the gas-driven piston assembly includes a flexible pushrod, a cylinder, and a piston. The flexible pushrod is workingly coupled with the plunger. The non-linear guide pathway at least partially surrounds the flexible pushrod. The cylinder has a gas inlet configured to be at least selectively in fluid communication with the gas chamber and a bore at least partially surrounding the flexible pushrod. The piston is in operable communication with the flexible pushrod and moveable within the bore of the cylinder in response to the pressurized gas entering the cylinder through the gas inlet.

Other aspects of the present disclosure include a gas-driven drug delivery device comprising a drug container, a plunger, a gas chamber, and a piston assembly including a roller pushrod guide system having a non-linear guide pathway. The drug container has a drug outlet and is configured to contain a drug. The plunger is slidably coupled with the drug container. The gas chamber is configured to contain a pressurized gas. In addition to the roller pushrod guide system, the gas-driven piston assembly includes a flexible pushrod, a cylinder, and a piston. The flexible pushrod is workingly coupled with the plunger. The cylinder has a gas inlet configured to be at least selectively in fluid communication with the gas chamber and a bore at least partially surrounding the flexible pushrod. The piston is in operable communication with the flexible pushrod and moveable within the bore of the cylinder in response to the pressurized gas entering the cylinder through the gas inlet. The roller pushrod guide system includes the non-linear guide pathway, a center roller, a first pinch roller, and a second pinch roller. The non-linear guide pathway includes at least a first portion located between the first pinch roller and the center roller and a second portion located between the second pinch roller and the center roller.

Yet other aspects of the present disclosure include a gas-driven drug delivery device comprising a drug container, a plunger, a gas chamber, and a piston assembly having a gear pushrod system including a non-linear guide pathway. The drug container has a drug outlet and is configured to contain a drug. The plunger is slidably coupled with the drug container. The gas chamber is configured to contain a pressurized gas. In addition to the roller pushrod guide system, the gas-driven piston assembly includes a flexible pushrod, a cylinder, and a piston. The flexible pushrod is workingly coupled with the plunger. The cylinder has a gas inlet configured to be at least selectively in fluid communication with the gas chamber and a bore at least partially surrounding the flexible pushrod. The piston is in operable communication with the flexible pushrod and moveable within the bore of the cylinder in response to the pressurized gas entering the cylinder through the gas inlet. The gear pushrod system includes a center roller with an attached center gear, a first pinch roller with an attached first pinch gear, and a second pinch roller with an attached second pinch gear. The non-linear guide pathway includes at least a first portion located between the first pinch roller and the center roller and a second portion located between the second pinch roller and the center roller, the first pinch gear operably engaged with the center gear, and the center gear operably engaged with the second pinch gear.

The drug container may have a longitudinal axis between the drug outlet and the plunger. In some forms, the bore of the cylinder may be parallel to the longitudinal axis of the drug container. In other forms, the bore of the cylinder may be perpendicular to the longitudinal axis of the drug container.

In some forms, the bore of the cylinder may have a bore diameter, the flexible pushrod may have a pushrod diameter, and the bore diameter may be greater than the pushrod diameter. In some forms, the plunger may have a plunger diameter and the piston may have a piston diameter that is less than or equal to the plunger diameter.

In some forms, the gas-driven piston assembly may further include a pushrod support between the piston and the flexible pushrod.

In some forms, the flexible pushrod may be made from at least one of pre-tensioned stainless steel extension spring stock, wire rope, and polymer tubing.

In some forms, the non-linear guide pathway may have a uniform curvature. On other forms, non-linear guide pathway may have a variable curvature.

In some forms, the non-linear guide pathway may have an interior surface including a low-friction material. The non-linear guide may have a pushrod inlet. The pushrod inlet may have a chamfered edge. The non-linear guide may have a pushrod outlet. A bushing may be located at the pushrod outlet.

In some forms, a plunger coupling is in operable communication with the plunger. In some forms, the plunger coupling may have a plunger connection projection that is received within a recess in a proximal face of a plunger. In other forms, the plunger coupling may have a foot, the foot in operable communication with the plunger and configured to distribute an output force from the flexible pushrod across a proximal face of the plunger. The plunger coupling may have a pushrod connection projection connected to an interior of the flexible pushrod.

In some forms, the center roller may have an outer surface including a high friction material. The center roller may have an outer surface with an interlocking geometry. The flexible pushrod may have an outer surface with an interlocking geometry. The outer surface of the center roller may interlock with the outer surface of the flexible pushrod.

The roller pushrod guide system may further include a rear support for the flexible pushrod. In some forms, the rear support may be static during operation of the gas-driven drug delivery device. In other forms, the rear support may be part of a pulley system. At least one of the center roller, the first pinch roller, and the second pinch roller may have low-friction bearings.

In some forms, the container has a cross-sectional area, the bore of the cylinder has a cross-sectional area, and the ratio of the cross-sectional area of the bore to the cross-sectional area of the container is determined by at least one of a limit of fluid pressure within the container and a desired flow rate to be achieved. The ratio of the cross-sectional area of the bore to the cross-sectional area of the container may further depend on fluid properties of a drug in the drug container.

In some forms, fluid pressure within the primary container determines a maximum allowable force to be exerted on the drug container.

In some forms, the piston assembly may be configured to allow the pressurized gas to be selectively vented.

In some forms, the gear pushrod guide system may have a gear efficiency equal to or greater than 95%. The center gear, the first pinch gear, and the second pinch gear may each have teeth. The number of teeth on the center gear, the first pinch gear, and the second pinch gear may be equal. The center gear, the first pinch gear, and the second pinch gear may each have a drive diameter. The drive diameters of the center gear, the first pinch gear, and the second pinch gear may be equal.

BRIEF DESCRIPTION OF THE DRAWINGS

The above needs are at least partially met through provision of the embodiments described in the following detailed description, particularly when studied in conjunction with the drawings, wherein.

Skilled artisans will appreciate that elements in the figures are illustrated for simplicity and clarity and have not necessarily been drawn to scale. For example, the dimensions and/or relative positioning of some of the elements in the figures may be exaggerated relative to other elements to help to improve understanding of various embodiments of the present invention. Also, common but well-understood elements that are useful or necessary in a commercially feasible embodiment are often not depicted in order to facilitate a less obstructed view of these various embodiments. It will further be appreciated that certain actions and/or steps may be described or depicted in a particular order of occurrence while those skilled in the art will understand that such specificity with respect to sequence is not actually required. It will also be understood that the terms and expressions used herein have the ordinary technical meaning as is accorded to such terms and expressions by persons skilled in the technical field as set forth above except where different specific meanings have otherwise been set forth herein.

DETAILED DESCRIPTION

A drug delivery system having a flexible piston assembly is provided that allows a variety of compact configurations of a drug delivery device that are not possible using traditional in-line piston designs or direct plunger drive designs due to the size constraints associated with such designs. Further, the flexible piston assembly isolates the driving gas from the primary drug container, reducing the risk of gas breaching the plunger and entering the drug product. In addition, the flexible piston assembly is designed to ensure that the fluid pressure within a primary container is at a safe level that protects the primary container from any failure as well as ensures a desired delivery rate.

Figure 1:
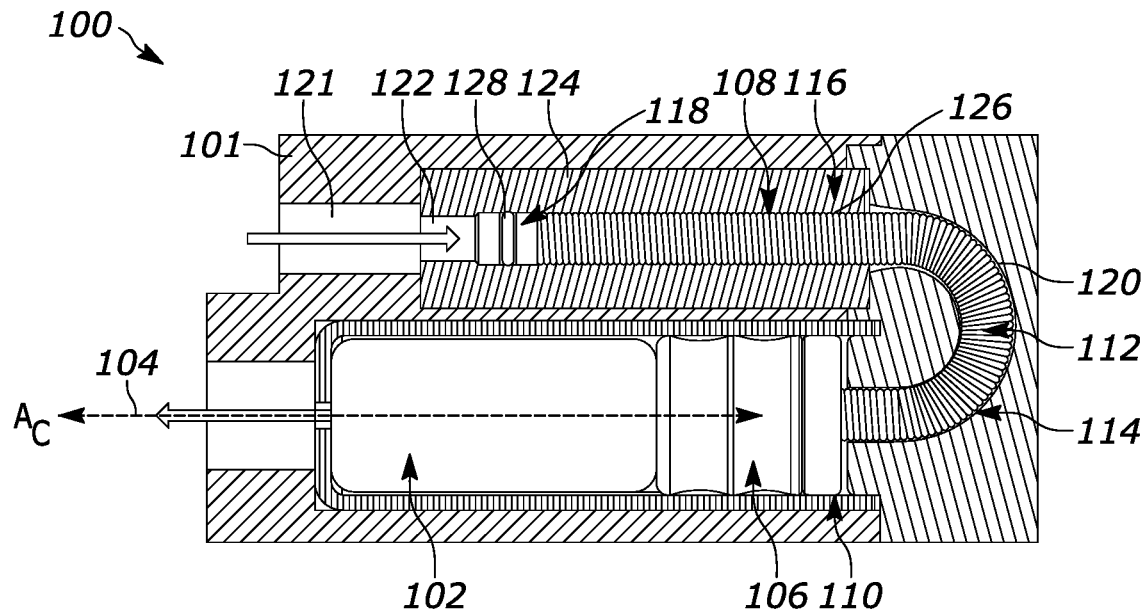
FIG. 1 is a cross-sectional view of a first exemplary embodiment of a drug delivery device comprising a flexible piston assembly and a stationary non-linear guide, the drug delivery device shown prior to drug delivery.
Figure 2:
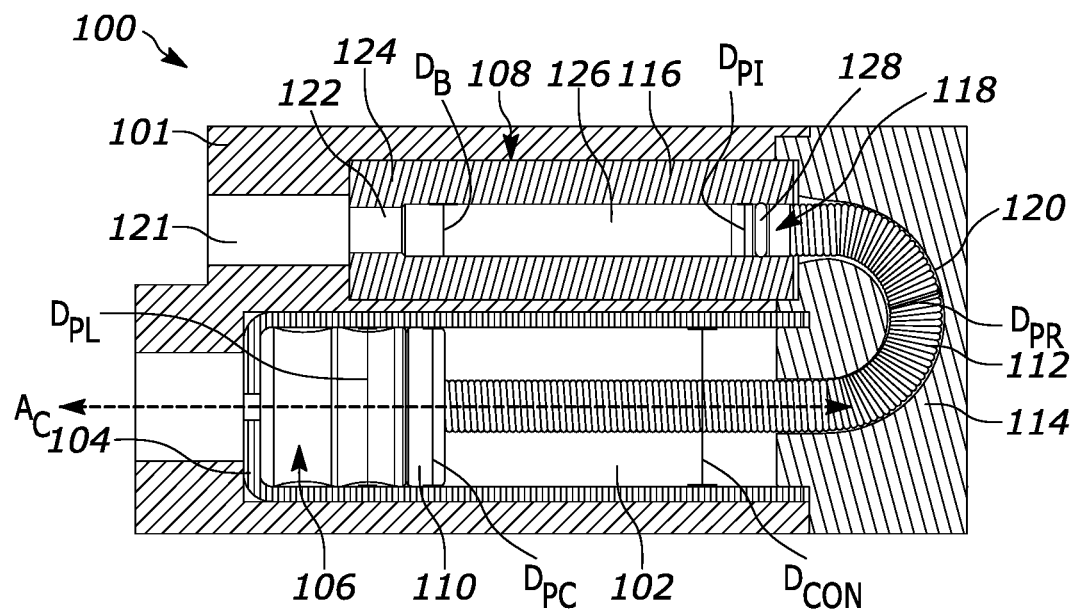
FIG. 2 is a cross-sectional view of the first exemplary embodiment of a drug delivery device of FIG. 1 after drug delivery.

Referring now to the drawings, and in particular to FIGS. 1 and 2, one generalized example of a gas-driven drug delivery device 100 is provided. The delivery device 100 includes a housing 101 which holds a drug container 102 that is configured to contain a drug. The drug container 102 includes a drug outlet 104. A plunger 106 is slidably coupled with the drug container 102 to expel the drug through the drug outlet 104. The housing 101 also holds a gas-driven piston assembly 108 that is connected to the plunger 106 by a flexible pushrod 112, which is further connected to a plunger coupling 110 in communication with the plunger 106. The gas-driven piston assembly 108 includes a flexible pushrod 112, a non-linear guide 114, a cylinder 116, and a piston 118.

Specifically, the plunger coupling 110 is connected to the flexible pushrod 112 of the gas-driven piston assembly 108. The flexible pushrod 112 is at least partially surrounded by a non-linear guide pathway 120 of the non-linear guide 114. Further, the flexible pushrod 112 is at least partially surrounded by the cylinder 116. The cylinder 116 includes a gas inlet 122, a cylinder body 124, and a bore 126 in the cylinder body 124. Finally, the flexible pushrod 112 is operably connected to the piston 118, as will be described below in relation to FIG. 3.

FIG. 1 shows the drug delivery device 100 prior to drug delivery. A gas chamber 121 is configured to receive and contain a pressurized gas. During drug delivery, the pressurized gas flows in the direction of the arrow depicted in FIG. 1 from the gas chamber 121 into the gas-driven piston assembly 108 through the gas inlet 122 of the cylinder 116. In response to the pressure created by gas entering the cylinder 116, the piston 118 moves within the bore 126 of the cylinder 116 and exerts a force on the flexible pushrod 112. As a result, the flexible pushrod 112 then exerts a force on the plunger coupling 110 and thus the plunger 106. The plunger 106 consequently moves through the container 102, forcing the drug in the container 102 to be expelled through the drug outlet 104 in the direction of the arrow depicted at the outlet 104 in FIG. 1. The plunger 106 ultimately stops moving adjacent to the drug outlet 104 after all of the drug has been expelled, as shown in FIG. 2.

In the arrangements shown in FIGS. 1 and 2, the bore 126 of the cylinder 116 is parallel to a longitudinal axis AC of the container 102. In other arrangements not herein depicted, the bore 126 of the cylinder may be perpendicular to or otherwise disposed at an angle transverse to the longitudinal axis AC of the container 102. As shown in FIG. 2, the bore 126 of the cylinder 116 has a bore diameter DB and the flexible pushrod 112 has a pushrod diameter DPR. The bore diameter DB and the pushrod diameter DPR are sized and configured to allow the flexible pushrod 112 to travel through the bore 126 of the cylinder 116. Bore 126 may comprise low friction materials to minimize drag forces on the flexible pushrod 112. The bore diameter DB is greater than the pushrod diameter DPR, which also prevents the flexible pushrod 112 from rubbing against, engaging, and/or scratching the bore 126 as the flexible pushrod 112 moves through the bore 126. The plunger 106 has a plunger diameter DPL, and the piston 118 has a piston diameter DPI. The piston diameter DPI is less than the bore diameter DB, This allows the piston 118 to travel through the bore 126 without scratching the bore 126 and to convert the input gas pressure into a controlled force on the flexible pushrod 112. The piston diameter DPI may be less than or greater than the plunger diameter DPL. This allows better control over the speed of drug delivery. In the example shown, the piston diameter DPI is less than the plunger diameter DPL.

Further, the plunger coupling 110 has a diameter DPC and the container 102 has an inner diameter DCON The diameter DPC is less than the plunger diameter DPL and is also less than an inner diameter DCON of the container 102 The container 102 has a cross-sectional area calculated based on DCON. The bore 126 of the cylinder 116 has a cross-sectional area calculated based on bore diameter DB. The ratio of the cross-sectional area of the container 102 to the cross-sectional area of the bore 126 is determined by at least one of a limit of fluid pressure within the container 102 and a desired flow rate to be achieved. That is, the ratio is chosen so that the failure limit of the container 102 (e.g., the pressure at which the container would fail) is not exceeded and/or to allow a drug to be expelled from the container 102 at a desired rate. Relevant factors in selecting the limit of fluid pressure are the initial pressure of the gas power source, physical parameters of the drug product such as viscosity, ambient design temperature, any measured resistance forces of the flexible pushrod 112 as it traverses through non-linear guide pathway 120, and desired flow rate achieved through drug outlet 104.

Figure 3:
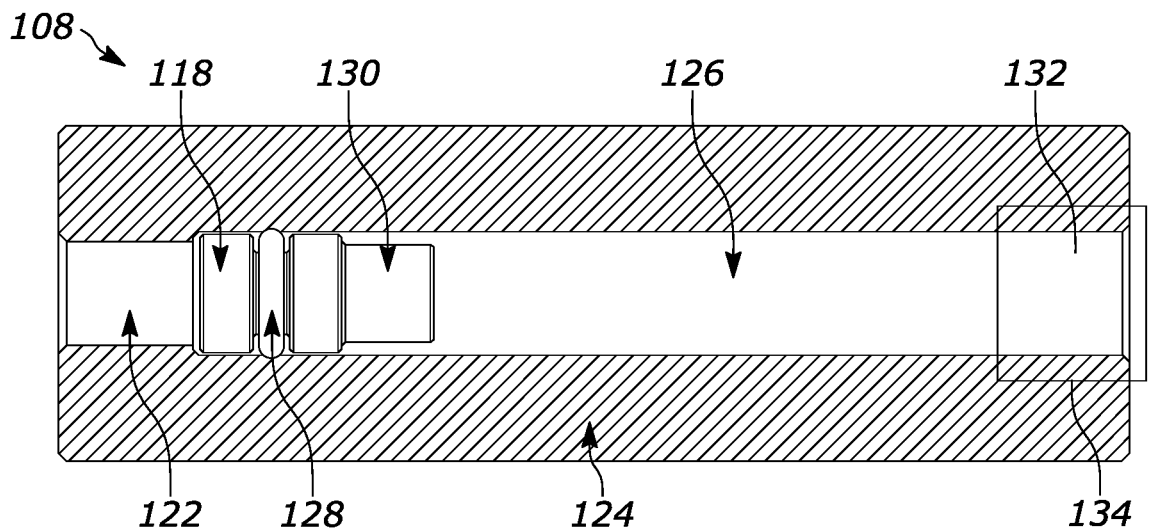
FIG. 3 is a cross-sectional view of the piston assembly of the first exemplary embodiment of a drug delivery device of FIGS. 1 and 2.

FIG. 3 illustrates additional details about the gas-driven piston assembly 108. The piston assembly 108 includes a piston seal 128 around the piston 118 within the bore 126. The piston seal 128 can be an O-ring or other type of sealing gasket, for example, that sealingly engages the cylinder body 124 such that compressed gas entering the bore 126 is restricted from passing beyond the piston 118. The bore 126 is smooth and is sized to produce the desired cylinder output force corresponding to the desired dispensing pressure within the container 102. That is, as the gas enters the gas inlet 122 of the cylinder 116, it is received within the bore 126 where it exerts pressure against the piston 118 and piston seal 128. This pressure causes the piston 118 to move, thereby generating a cylinder output force, which is exerted against the flexible pushrod 112 and ultimately against the plunger 106 as was shown previously in FIG. 1. This cylinder output force then acts against the plunger 106, causing a dispensing pressure within the container 102 and the drug to be dispensed as the plunger 106 advances. Thus, the cylinder output force is correlated with the dispensing pressure within the container 102. The cylinder output force is dependent upon the size of the bore 126 and the pressure of the gas within the bore 126. Accordingly, the size of the bore 126 impacts the dispensing pressure within the container 102. The size of the bore 126 can be chosen to help achieve a desired dispensing pressure within the container 102.

Put another way, the gas-driven piston assembly 108 is a first hydraulic subassembly. According to Pascal's principle, a change in pressure applied to an enclosed fluid is transmitted undiminished to all portions of the fluid and to the walls of the container. Accordingly, the cylinder output force is equivalent to the pressure of the compressed gas in the bore 126 multiplied by the cross-sectional area of the bore 126. Assuming the pressure of the compressed gas is unchanged, increasing the cross-sectional area of the bore 126 (and, as a result, the cross-sectional area of piston 118) increases the cylinder output force, and decreasing the cross-sectional area of the bore 126 decreases the cylinder output force. The cylinder output force is transmitted by the pushrod 112 to a second hydraulic subassembly that includes the plunger 106 and the container 102. According to Pascal's principle, the cylinder output force creates a pressure within the container 102 that is equivalent to the cylinder output force divided by the cross-sectional area of the plunger 106. Assuming the cross-sectional area of the plunger 106 is unchanged, increasing the cylinder output force increases the pressure within the container 102 and decreasing the cylinder output force decreases the pressure within the container 102. Linking the relationship between the first hydraulic subassembly and the second hydraulic subassembly, assuming the pressure of the compressed gas in the bore 126 and cross-sectional area of the plunger 106 are unchanged, the cross-sectional area of the bore 126 and the pressure within the container 102 are directly related. That is, increasing the cross-sectional area of the bore 126 increases the dispensing pressure within the container 102, and decreasing the cross-sectional area of the bore 126 decreases the dispensing pressure within the container 102, thereby allowing the assembly 108 to step-down pressure and/or be utilized as a pressure regulator.

A pushrod support 130 is provided between the piston 118 and the flexible pushrod 112 (not pictured). The pushrod support 130 maintains co-axial alignment of the piston 118 and the flexible pushrod 112 and increases the resistance of the flexible pushrod 112 to buckling. Specifically, at least a portion of the pushrod support 130 may be inserted into the flexible pushrod 112 and may extend for a distance axially within the flexible pushrod 112. The placement of the pushrod support 130 within the flexible pushrod 112 restricts some movement of the flexible pushrod 112, forcing the flexible pushrod 112 to stay co-axially aligned with the piston 118 at least in the section through which the pushrod support 130 extends. Further, the presence of the pushrod support 130 in the interior of the flexible pushrod 112 prevents buckling or warping in the area closest to the piston 118 when the piston 118 exerts a force on the flexible pushrod 112.

The bore 126 has an outlet 132. A bushing 134 may be provided at the bore outlet 132. The bushing 134 may engage the flexible pushrod 112. The bushing 134 reduces the friction between the outlet 132 of the bore 126 and the flexible pushrod 112. Reducing the friction allows the cylinder output force to be more efficiently transmitted through the flexible pushrod 112 to the plunger 106. Further, the bushing 134 may help to reduce wear that would otherwise be caused by contact between the outlet 132 of the bore 126 and the flexible pushrod 112.

Depending on environmental conditions, such as temperature or ambient pressure, and as a result of variability in initial pressures of the gas power source, the gas pressure in the gas-driven piston assembly 108 may exceed a pressure tolerance limit of the container 102. For example, pressures exceeding 100 psi on the piston 118 may cause failure of the container 102, particularly if the container 102 is made of glass. This over-pressure condition may also occur as a result of variability in drug product viscosity, which may cause pressure spikes within the container 102. To avoid damage to the container 102, the piston seal 128 can be designed to allow excess pressure to be selectively vented out before such high pressures affect the container 102. Alternatively, pressure relief components such as over-pressure valves may be provided before the piston 118 or at other locations within the gas-driven piston assembly 108 to selectively vent excess pressure. As a result, a force exerted upon the plunger 106 is reduced by the piston assembly 108 prior to being applied to the plunger 106 so that the plunger 106 exerts less than or equal to a maximum allowable force on the drug container. These pressure relief features may also allow end of dose pressure relief by venting excess pressure to the atmosphere. These pressure relief features may also be a solution for managing highly variable input pressure while still yielding more predictable output pressure and thereby drug delivery time.

Figure 4:
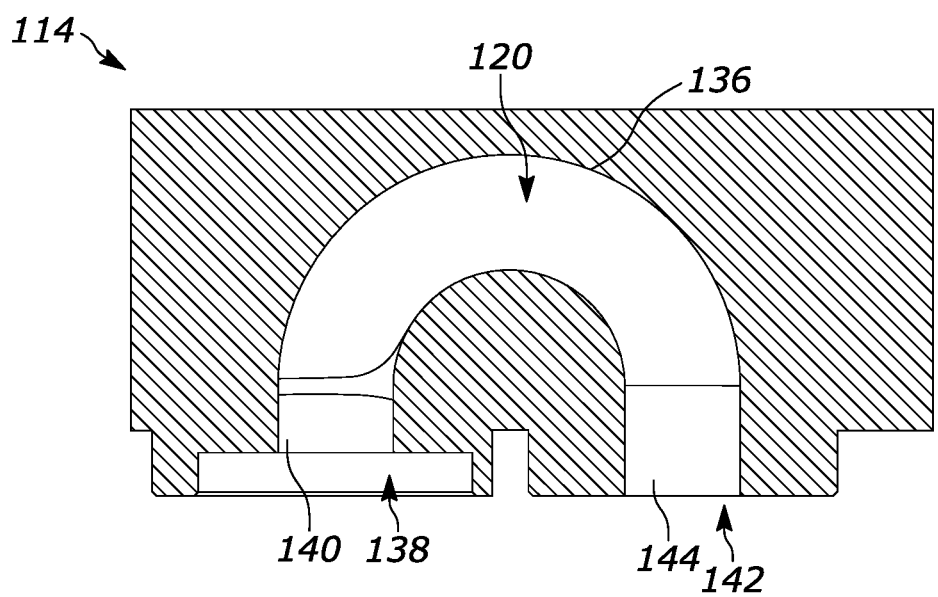
FIG. 4 is a cross-sectional view of the non-linear guide of the first exemplary embodiment of a drug delivery device of FIGS. 1 and 2.

FIG. 4 illustrates additional details about the non-linear guide 114. In the arrangement shown in FIG. 4, the non-linear guide 114 is static and uses no moving parts to guide the flexible pushrod 112 through the non-linear guide pathway 120. The non-linear guide pathway 120 is shown as being configured to fully encircle the flexible pushrod 112. However, the non-linear guide pathway 120 may in alternate arrangements only partially cover and/or support the flexible pushrod 112. The non-linear guide pathway may have a uniform cross-section or may have a variable cross-section to accommodate, for example, a tapered or otherwise shaped flexible pushrod 112. The non-linear guide pathway 120 may have a constant or varying curvature or radius, for example, as may be required for the desired application. In the depicted version, the non-linear guide pathway 120 has a generally U-shape due to the orientation of the bore 126 relative to the container 102. But for drug delivery devices with different form factors, for example, the non-linear guide pathway 120 could be C-shaped, S-shaped, J-shaped, or any other suitable shape for the intended application.

The flexible pushrod 112 may be made from at least one of pre-tensioned stainless steel extension spring stock, wire rope, polymer tubing, or other suitable material. The flexible pushrod 112 may be made from any material that is axially rigid but laterally flexible. The flexible pushrod 112 may be a single pushrod or may alternately comprise multiple connected segments. Each segment may be made from a material that is axially rigid but laterally flexible, such as pre-tensioned stainless steel extension spring stock, wire rope, polymer tubing, or other suitable material. Alternately, each segment may be made from a rigid material without lateral flex and the interconnected nature of the segments may provide the necessary flexibility. Some arrangements may have a combination of rigid segments and segments having axial rigidity and lateral flexibility. Some segments may be entirely flexible without any axial rigidity but when combined with other segments, may provide sufficient structure to operate as part of the flexible pushrod 112.

The non-linear guide pathway 120 may have an interior surface 136 that is made of a lubricious or low-friction material, such as Teflon®. Alternately, the flexible pushrod 112 may be coated with a lubricious or low-friction material. As yet another option, the non-linear guide pathway 120 or the flexible pushrod 112 may be sprayed during manufacturing with a lubricating fluid, such as an oil, to facilitate movement of the flexible pushrod 112 within the non-linear guide pathway 120. The non-linear guide 114 includes a pushrod inlet 138 and a pushrod outlet 142. The pushrod inlet 138 includes an edge 140*m* which can be chamfered in certain versions, to prevent catching or binding of the flexible pushrod 112. Having the flexible pushrod 112 bind or catch on the non-linear guide 114 would prevent the flexible pushrod 112 from fully transferring the cylinder output force to the plunger 106 and could damage either the flexible pushrod 112 or the non-linear guide 114. A bushing 144 may be provided at the pushrod outlet 142 as a feature of the non-linear guide pathway 120 or as a separate component. The bushing 144 may engage the flexible pushrod 112. The bushing 144 reduces the friction between the pushrod outlet 142 of the non-linear guide 114 and the flexible pushrod 112. Reducing the friction allows the cylinder output force to be more efficiently transmitted through the flexible pushrod 112 to the plunger 106. Further, the bushing 142 may help to reduce wear that would otherwise be caused by contact between the pushrod outlet 142 of the non-linear guide 114 and the flexible pushrod 112.

Figure 5A:
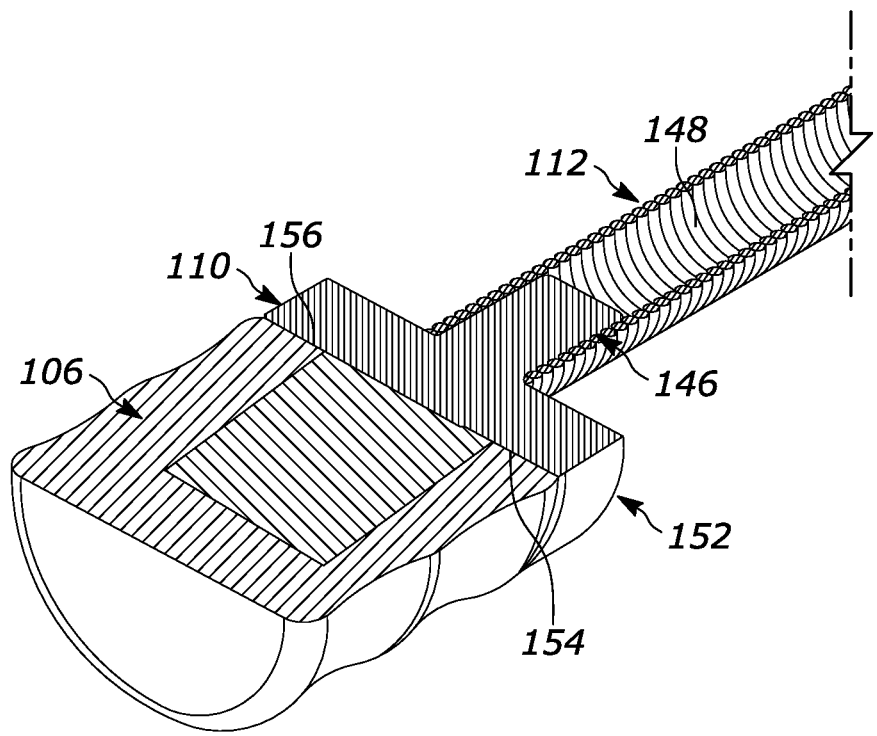
FIG. 5A is a cross-sectional view of a second embodiment of a plunger coupling having a foot.
Figure 5B:
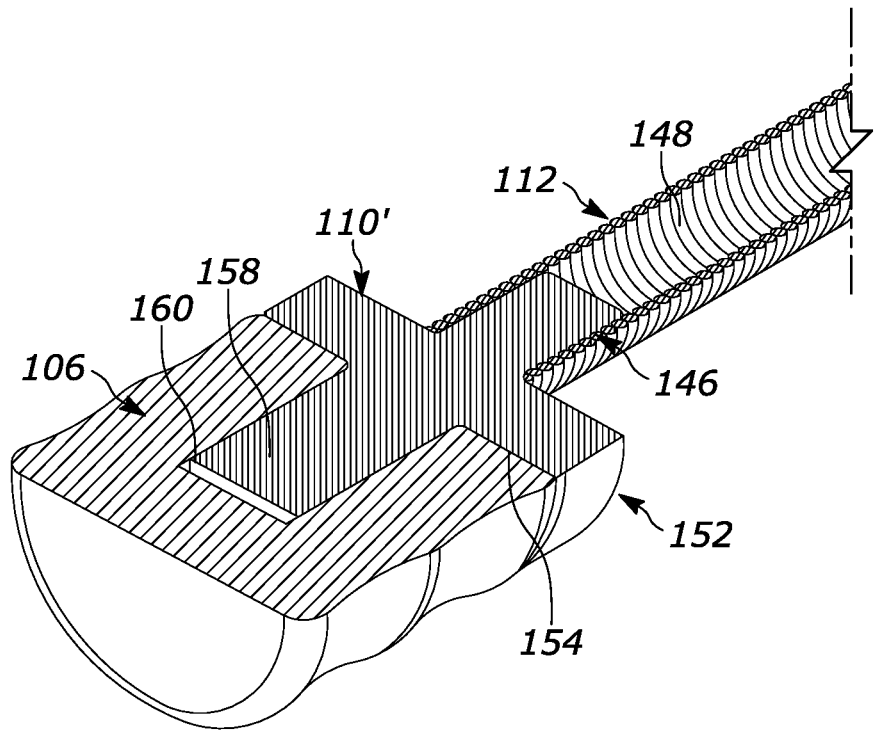
FIG. 5B is a cross-sectional view a first embodiment of a plunger coupling having a plunger connection projection.

FIGS. 5A and 5B illustrate two alternate versions of a plunger coupling (identified as 108 and 108'). In both FIGS. 5A and 5B, the plunger coupling 110 and 110' includes a pushrod connection projection 146 that connects to an interior 148 of the flexible pushrod 112. Further, the plunger coupling 110 and 110' both have a foot 152 that makes contact with a proximal face 154 of the plunger 106. In FIG. 5A, the foot 152 has a flat surface 156 that is configured to distribute an output force from the flexible pushrod 112 across the proximal face 154 of the plunger 106. In FIG. 5B, the plunger coupling 110' further includes a pushrod connection projection 158 that is received in a recess 160 in the proximal face 154 of the plunger 106. Either configuration is suitable.

Figure 6:
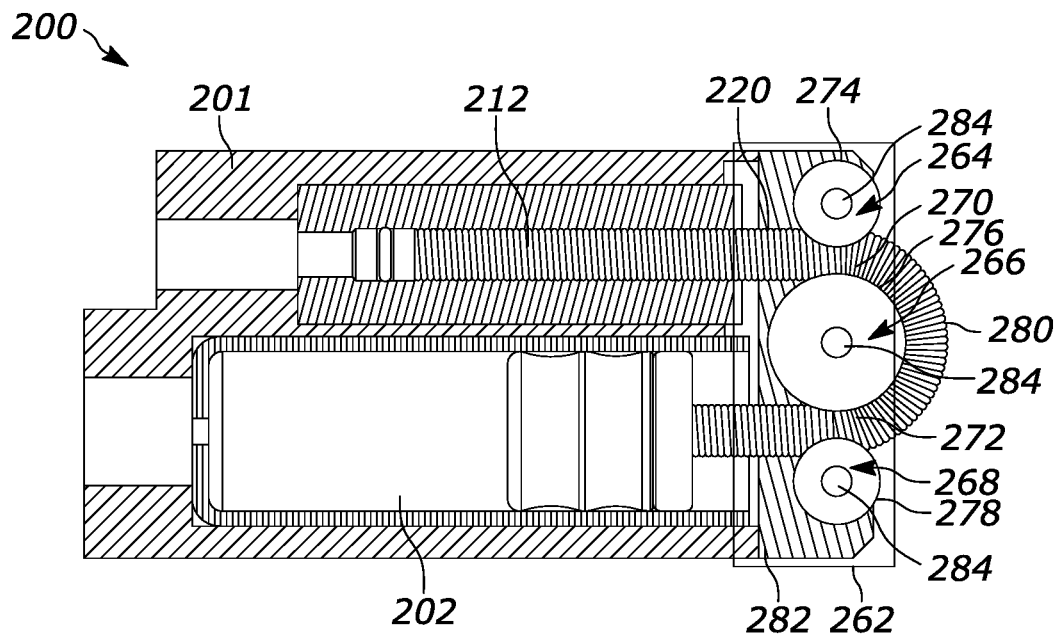
FIG. 6 is a cross-sectional view of a second exemplary embodiment of a drug delivery device comprising a flexible piston assembly and a roller pushrod guide system.
Figure 7:
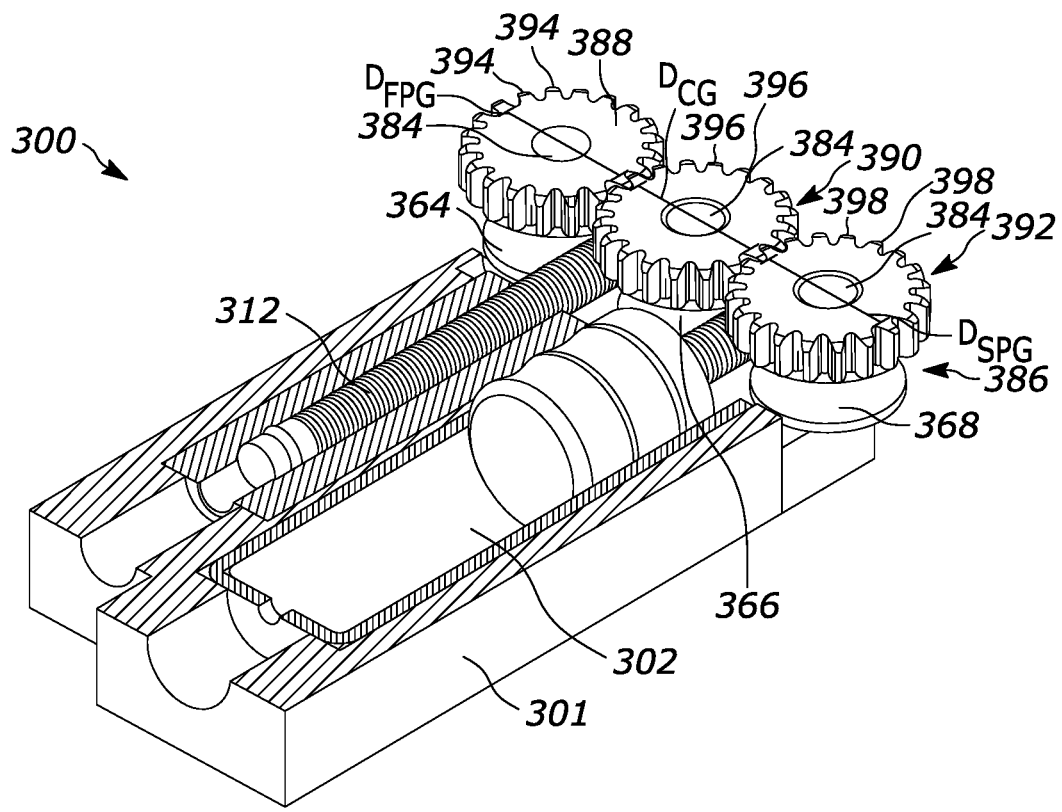
FIG. 7 is a cross-sectional view of a third embodiment of a drug delivery device comprising a flexible piston assembly and a gear pushrod guide system.

FIGS. 6 and 7 depict gas-driven drug delivery devices 200 and 300 sharing many features described with respect to drug delivery device 100. Interchangeable features are identified by the same reference number increased by a multiple of 100. For example, the same drug container can be used in all arrangements and is identified as drug container 102 in FIGS. 1 and 2, drug container 202 in FIG. 6, and drug container 302 in FIG. 7. Unless otherwise stated, the description provided with respect to an interchangeable feature in one arrangement applies equally to the corresponding interchangeable feature in another arrangement.

The gas-driven drug delivery device 200 of FIG. 6 includes a roller pushrod guide system 262. The roller pushrod guide system 262 includes a first pinch roller 264, a center roller 266, and a second pinch roller 268. The flexible pushrod 212 travels through the roller pushrod guide system 262 along the non-linear guide pathway 220. The non-linear guide pathway 220 includes a first portion 270 located between the first pinch roller 264 and the center roller 266 and a second portion 272 located between the second pinch roller 268 and the center roller 266.

In order to ensure that the flexible pushrod 212 is adequately engaged with the roller pushrod guide system 262, an outer surface 274 of the first pinch roller 264, an outer surface 276 of the center roller 266, and/or an outer surface 278 of the second pinch roller 268 may include a high friction material, such as polyurethane with a hardness of Shore A 80-90. Alternately, or in addition, the flexible pushrod 212 may have an outer surface 280 with an interlocking geometry. The outer surface 276 of the center roller 266, the outer surface 274 of the first pinch roller 264, and/or the outer surface 278 of the second pinch roller 268 may also have an interlocking geometry configured to interlock with the outer surface 280 of the flexible pushrod 212. For example, the outer surface 280 of the flexible pushrod 212 may have a series of circumferential ridges that are received into complementary valleys located on the outer surface 276 of the center roller 266, the outer surface 274 of the first pinch roller 264, and/or the outer surface 278 of the second pinch roller 268. The engagement between the ridges and the valleys may prevent slipping and facilitate efficient movement of the flexible pushrod 212 through the roller pushrod guide system 262. Other complementary interlocking geometries are also possible, including but not limited to complementary projections and recesses, interlocking raised complementary tessellations, and adjacent linear ribs.

In addition, the roller pushrod guide system 262 may include a rear support 282 for the flexible pushrod 212. The rear support 282 may be static during operation, providing a stationary mounting surface for the first pinch roller 264, second pinch roller 268, and center roller 266. Alternately, the rear support 282 of the drug delivery device 200 may move as part of a pulley system configured to assist with movement of the flexible pushrod 212. For example, the rear support 282 may be a pulley cord engaged with at least one of the first pinch roller 264, second pinch roller 268, and center roller 266, and a force may be applied to the rear support 282 to encourage rotation of the connected component(s) and thus facilitate movement of the flexible pushrod 212. The first pinch roller 264, center roller 266, and/or second pinch roller 268 may each have low friction bearings 284 to achieve high mechanical drive efficiency.

The gas-driven drug delivery device 300 of FIG. 7 includes a gear pushrod guide system 386. The gear pushrod guide system 386 includes a first pinch gear 388 attached to the first pinch roller 364, a center gear 390 attached to the center roller 366, and a second pinch gear 392 attached to the second pinch roller 368. The first pinch gear 388, center gear 390, and second pinch gear 392 all have respective teeth 394, 396, and 398 to engage with one another. The first pinch gear 388 is operably engaged with the center gear 390, and the center gear 390 is operably engaged with the second pinch gear 392. The drug delivery device 300 may, in addition to having a gas drive, include one or more motors connected to one or more of the first pinch gear 388, center gear 390, and second pinch gear 392. That is, the drug delivery device 300 may have an auxiliary drive system that is not gas-driven. Alternately, any or all of the first pinch gear 388, center gear 390, and second pinch gear 392 may be passive and not directly attached to a motor.

Regardless of how the gears 388, 390, and 392 are driven, the gear pushrod guide system 386 helps to coordinate movement of the flexible pushrod 312. The movement of one of the gears (for example, gear 388) causes movement of the other gears (390 and 392, for example). The corresponding rollers 364, 366, and 368 are moved as a result, and the flexible pushrod 312 is encouraged at multiple points of contact to move. This helps to prevent any one portion of the flexible pushrod 312 from becoming stuck. The gear pushrod guide system 386 minimizes any chance of slippage or buckling of the flexible pushrod 312 as the amount of translation of the flexible pushrod 312 is coordinated at multiple points of the flexible pushrod 312 with minimal backlash based on gear teeth and pitch geometrical tolerances.

The gear pushrod guide system 386 may have a gear efficiency equal to or greater than 95%. The first pinch roller 364, center roller 366, and/or second pinch roller 368 may each have low friction bearings 384 to achieve high mechanical drive efficiency. The number of teeth 394, 396, and 398 on, respectively, the first pinch gear 388, center gear 390, and second pinch gear 392 may be equal. The first pinch gear 388, center gear 390, and second pinch gear 392 have respective drive diameters DFPG, DCG, and DSPG, which may be equal.

The above description describes various devices, assemblies, components, subsystems and methods for use related to a drug delivery device. The devices, assemblies, components, subsystems, methods or drug delivery devices can further comprise or be used with a drug including but not limited to those drugs identified below as well as their generic and biosimilar counterparts. The term drug, as used herein, can be used interchangeably with other similar terms and can be used to refer to any type of medicament or therapeutic material including traditional and non-traditional pharmaceuticals, nutraceuticals, supplements, biologics, biologically active agents and compositions, large molecules, biosimilars, bioequivalents, therapeutic antibodies, polypeptides, proteins, small molecules and generics. Non-therapeutic injectable materials are also encompassed. The drug may be in liquid form, a lyophilized form, or in a reconstituted from lyophilized form. The following example list of drugs should not be considered as all-inclusive or limiting.

The drug will be contained in a reservoir. In some instances, the reservoir is a primary container that is either filled or pre-filled for treatment with the drug. The primary container can be a vial, a cartridge or a pre-filled syringe.

In some embodiments, the reservoir of the drug delivery device may be filled with or the device can be used with colony stimulating factors, such as granulocyte colony-stimulating factor (G-CSF). Such G-CSF agents include but are not limited to Neulasta® (pegfilgrastim, pegylated filgastrim, pegylated G-CSF, pegylated hu-Met-G-CSF) and Neupogen® (filgrastim, G-CSF, hu-MetG-CSF), UDENYCA® (pegfilgrastim-cbqv), Ziextenzo® (LA-EP2006; pegfilgrastim-bmez), or FULPHILA (pegfilgrastim-bmez).

In other embodiments, the drug delivery device may contain or be used with an erythropoiesis stimulating agent (ESA), which may be in liquid or lyophilized form. An ESA is any molecule that stimulates erythropoiesis. In some embodiments, an ESA is an erythropoiesis stimulating protein. As used herein, "erythropoiesis stimulating protein"

means any protein that directly or indirectly causes activation of the erythropoietin receptor, for example, by binding to and causing dimerization of the receptor. Erythropoiesis stimulating proteins include erythropoietin and variants, analogs, or derivatives thereof that bind to and activate erythropoietin receptor; antibodies that bind to erythropoietin receptor and activate the receptor; or peptides that bind to and activate erythropoietin receptor. Erythropoiesis stimulating proteins include, but are not limited to, Epogen® (epoetin alfa), Aranesp® (darbepoetin alfa), Dynepo® (epoetin delta), Mircera® (methoxy polyethylene glycol-epoetin beta), Hematide®, MRK-2578, INS-22, Retacrit® (epoetin zeta), Neorecormon® (epoetin beta), Silapo® (epoetin zeta), Binocrit® (epoetin alfa), epoetin alfa Hexal, Abseamed® (epoetin alfa), Ratioepo® (epoetin theta), Eporatio® (epoetin theta), Biopoin® (epoetin theta), epoetin alfa, epoetin beta, epoetin iota, epoetin omega, epoetin delta, epoetin zeta, epoetin theta, and epoetin delta, pegylated erythropoietin, carbamylated erythropoietin, as well as the molecules or variants or analogs thereof.

Among particular illustrative proteins are the specific proteins set forth below, including fusions, fragments, analogs, variants or derivatives thereof: OPGL specific antibodies, peptibodies, related proteins, and the like (also referred to as RANKL specific antibodies, peptibodies and the like), including fully humanized and human OPGL specific antibodies, particularly fully humanized monoclonal antibodies; Myostatin binding proteins, peptibodies, related proteins, and the like, including myostatin specific peptibodies; IL-4 receptor specific antibodies, peptibodies, related proteins, and the like, particularly those that inhibit activities mediated by binding of IL-4 and/or IL-13 to the receptor; Interleukin 1-receptor 1 ("IL1-R1") specific antibodies, peptibodies, related proteins, and the like; Ang2 specific antibodies, peptibodies, related proteins, and the like; NGF specific antibodies, peptibodies, related proteins, and the like; CD22 specific antibodies, peptibodies, related proteins, and the like, particularly human CD22 specific antibodies, such as but not limited to humanized and fully human antibodies, including but not limited to humanized and fully human monoclonal antibodies, particularly including but not limited to human CD22 specific IgG antibodies, such as, a dimer of a human-mouse monoclonal hLL2 gamma-chain disulfide linked to a human-mouse monoclonal hLL2 kappa-chain, for example, the human CD22 specific fully humanized antibody in Epratuzumab, CAS registry number 501423-23-0; IGF-1 receptor specific antibodies, peptibodies, and related proteins, and the like including but not limited to anti-IGF-1R antibodies; B-7 related protein 1 specific antibodies, peptibodies, related proteins and the like ("B7RP-1" and also referring to B7H2, ICOSL, B7h, and CD275), including but not limited to B7RP-specific fully human monoclonal IgG2 antibodies, including but not limited to fully human IgG2 monoclonal antibody that binds an epitope in the first immunoglobulin-like domain of B7RP-1, including but not limited to those that inhibit the interaction of B7RP-1 with its natural receptor, ICOS, on activated T cells; IL-15 specific antibodies, peptibodies, related proteins, and the like, such as, in particular, humanized monoclonal antibodies, including but not limited to HuMax IL-15 antibodies and related proteins, such as, for instance, 145c7; IFN gamma specific antibodies, peptibodies, related proteins and the like, including but not limited to human IFN gamma specific antibodies, and including but not limited to fully human anti-IFN gamma antibodies; TALL-1 specific antibodies, peptibodies, related proteins, and the like, and other TALL specific binding proteins; Parathyroid hormone ("PTH") specific antibodies, peptibodies, related proteins, and the like; Thrombopoietin receptor ("TPO-R") specific antibodies, peptibodies, related proteins, and the like; Hepatocyte growth factor ("HGF") specific antibodies, peptibodies, related proteins, and the like, including those that target the HGF/SF:cMet axis (HGF/SF:c-Met), such as fully human monoclonal antibodies that neutralize hepatocyte growth factor/scatter (HGF/SF); TRAIL-R2 specific antibodies, peptibodies, related proteins and the like; Activin A specific antibodies, peptibodies, proteins, and the like; TGF-beta specific antibodies, peptibodies, related proteins, and the like; Amyloid-beta protein specific antibodies, peptibodies, related proteins, and the like; c-Kit specific antibodies, peptibodies, related proteins, and the like, including but not limited to proteins that bind c-Kit and/or other stem cell factor receptors; OX40L specific antibodies, peptibodies, related proteins, and the like, including but not limited to proteins that bind OX40L and/or other ligands of the OX40 receptor; Activase® (alteplase, tPA); Aranesp® (darbepoetin alfa) Erythropoietin [30-asparagine, 32-threonine, 87-valine, 88-asparagine, 90-threonine], Darbepoetin alfa, novel erythropoiesis stimulating protein (NESP); Epogen® (epoetin alfa, or erythropoietin); GLP-1, Avonex® (interferon beta-1a); Bexxar® (tositumomab, anti-CD22 monoclonal antibody); Betaseron® (interferon-beta); Campath® (alemtuzumab, anti-CD52 monoclonal antibody); Dynepo® (epoetin delta); Velcade® (bortezomib); MLN0002 (anti-α4I37 mAb); MLN1202 (anti-CCR2 chemokine receptor mAb); Enbrel® (etanercept, TNF-receptor/Fc fusion protein, TNF blocker); Eprex® (epoetin alfa); Erbitux® (cetuximab, anti-EGFR/HER1/c-ErbB-1); Genotropin® (somatropin, Human Growth Hormone); Herceptin® (trastuzumab, anti-HER2/neu (erbB2) receptor mAb); Kanjinti™ (trastuzumab-anns) anti-HER2 monoclonal antibody, biosimilar to Herceptin®, or another product containing trastuzumab for the treatment of breast or gastric cancers; Humatrope® (somatropin, Human Growth Hormone); Humira® (adalimumab); Vectibix® (panitumumab), Xgeva® (denosumab), Prolia® (denosumab), Immunoglobulin G2 Human Monoclonal Antibody to RANK Ligand, Enbrel® (etanercept, TNF-receptor/Fc fusion protein, TNF blocker), Nplate® (romiplostim), rilotumumab, ganitumab, conatumumab, brodalumab, insulin in solution; Infergen® (interferon alfacon-1); Natrecor® (nesiritide; recombinant human B-type natriuretic peptide (hBNP); Kineret® (anakinra); Leukine® (sargamostim, rhuGM-CSF); LymphoCide® (epratuzumab, anti-CD22 mAb); Benlysta™ (lymphostat B, belimumab, anti-BlyS mAb); Metalyse® (tenecteplase, t-PA analog); Mircera® (methoxy polyethylene glycol-epoetin beta); Mylotarg® (gemtuzumab ozogamicin); Raptiva® (efalizumab); Cimzia® (certolizumab pegol, CDP 870); Solids™ (eculizumab); pexelizumab (anti-05 complement); Numax® (MEDI-524); Lucentis® (ranibizumab); Panorex® (17-1A, edrecolomab); Trabio® (lerdelimumab); TheraCim hR3 (nimotuzumab); Omnitarg (pertuzumab, 2C4); Osidem® (IDM-1); OvaRex® (B43.13); Nuvion® (visilizumab); cantuzumab mertansine (huC242-DM1); NeoRecormon® (epoetin beta); Neumega® (oprelvekin, human interleukin-11); Orthoclone OKT3® (muromonab-CD3, anti-CD3 monoclonal antibody); Procrit® (epoetin alfa); Remicade® (infliximab, anti-TNFα monoclonal antibody); Reopro® (abciximab, anti-GP IIb/IIIa receptor monoclonal antibody); Actemra® (anti-IL6 Receptor mAb); Avastin® (bevacizumab), HuMax-CD4 (zanolimumab); Mvasi™ (bevacizumab-awwb); Rituxan® (rituximab, anti-CD20 mAb); Tarceva® (erlotinib); Roferon-A®-(interferon alfa-2a); Simulect® (basiliximab);

Prexige® (lumiracoxib); Synagis® (palivizumab); 145c7-CHO (anti-IL15 antibody, see U.S. Pat. No. 7,153,507); Tysabri® (natalizumab, anti-α4integrin mAb); Valortim® (MDX-1303, anti-*B. anthracis* protective antigen mAb); ABthrax™ Xolair® (omalizumab); ETI211 (anti-MRSA mAb); IL-1 trap (the Fc portion of human IgG1 and the extracellular domains of both IL-1 receptor components (the Type I receptor and receptor accessory protein)); VEGF trap (Ig domains of VEGFR1 fused to IgG1 Fc); Zenapax® (daclizumab); Zenapax® (daclizumab, anti-IL-2Ra mAb); Zevalin® (ibritumomab tiuxetan); Zetia® (ezetimibe); Orencia® (atacicept, TACI-Ig); anti-CD80 monoclonal antibody (galiximab); anti-CD23 mAb (lumiliximab); BR2-Fc (huBR3/huFc fusion protein, soluble BAFF antagonist); CNTO 148 (golimumab, anti-TNFα mAb); HGS-ETR1 (mapatumumab; human anti-TRAIL Receptor-1 mAb); HuMax-CD20 (ocrelizumab, anti-CD20 human mAb); HuMax-EGFR (zalutumumab); M200 (volociximab, anti-α5β1 integrin mAb); MDX-010 (ipilimumab, anti-CTLA-4 mAb and VEGFR-1 (IMC-18F1); anti-BR3 mAb; anti-*C. difficile* Toxin A and Toxin B C mAbs MDX-066 (CDA-1) and MDX-1388); anti-CD22 dsFv-PE38 conjugates (CAT-3888 and CAT-8015); anti-CD25 mAb (HuMax-TAC); anti-CD3 mAb (NI-0401); adecatumumab; anti-CD30 mAb (MDX-060); MDX-1333 (anti-IFNAR); anti-CD38 mAb (HuMax CD38); anti-CD40L mAb; anti-Cripto mAb; anti-CTGF Idiopathic Pulmonary Fibrosis Phase I Fibrogen (FG-3019); anti-CTLA4 mAb; anti-eotaxin1 mAb (CAT-213); anti-FGF8 mAb; anti-ganglioside GD2 mAb; anti-ganglioside GM2 mAb; anti-GDF-8 human mAb (MYO-029); anti-GM-CSF Receptor mAb (CAM-3001); anti-HepC mAb (HuMax HepC); anti-IFNα mAb (MEDI-545, MDX-198); anti-IGF1R mAb; anti-IGF-1R mAb (HuMax-Inflam); anti-IL12 mAb (ABT-874); anti-IL12/IL23 mAb (CNTO 1275); anti-IL13 mAb (CAT-354); anti-IL2Ra mAb (HuMax-TAC); anti-IL5 Receptor mAb; anti-integrin receptors mAb (MDX-018, CNTO 95); anti-IP10 Ulcerative Colitis mAb (MDX-1100); BMS-66513; anti-Mannose Receptor/hCGβ mAb (MDX-1307); anti-mesothelin dsFv-PE38 conjugate (CAT-5001); anti-PD1mAb (MDX-1106 (ONO-4538)); anti-PDGFRa antibody (IMC-3G3); anti-TGFβ mAb (GC-1008); anti-TRAIL Receptor-2 human mAb (HGS-ETR2); anti-TWEAK mAb; anti-VEGFR/Flt-1 mAb; and anti-ZP3 mAb (HuMax-ZP3).

In some embodiments, the drug delivery device may contain or be used with a sclerostin antibody, such as but not limited to romosozumab, blosozumab, BPS 804 (Novartis), Evenity™ (romosozumab-aqqg), another product containing romosozumab for treatment of postmenopausal osteoporosis and/or fracture healing and in other embodiments, a monoclonal antibody (IgG) that binds human Proprotein Convertase Subtilisin/Kexin Type 9 (PCSK9). Such PCSK9 specific antibodies include, but are not limited to, Repatha® (evolocumab) and Praluent® (alirocumab). In other embodiments, the drug delivery device may contain or be used with rilotumumab, bixalomer, trebananib, ganitumab, conatumumab, motesanib diphosphate, brodalumab, vidupiprant or panitumumab. In some embodiments, the reservoir of the drug delivery device may be filled with or the device can be used with IMLYGIC® (talimogene laherparepvec) or another oncolytic HSV for the treatment of melanoma or other cancers including but are not limited to OncoV-EXGALV/CD; OrienX010; G207, 1716; NV1020; NV12023; NV1034; and NV1042. In some embodiments, the drug delivery device may contain or be used with endogenous tissue inhibitors of metalloproteinases (TIMPs) such as but not limited to TIMP-3. In some embodiments, the drug delivery device may contain or be used with Aimovig® (erenumab-aooe), anti-human CGRP-R (calcitonin gene-related peptide type 1 receptor) or another product containing erenumab for the treatment of migraine headaches. Antagonistic antibodies for human calcitonin gene-related peptide (CGRP) receptor such as but not limited to erenumab and bispecific antibody molecules that target the CGRP receptor and other headache targets may also be delivered with a drug delivery device of the present disclosure. Additionally, bispecific T cell engager (BITE®) antibodies such as but not limited to BLINCYTO® (blinatumomab) can be used in or with the drug delivery device of the present disclosure. In some embodiments, the drug delivery device may contain or be used with an APJ large molecule agonist such as but not limited to apelin or analogues thereof. In some embodiments, a therapeutically effective amount of an anti-thymic stromal lymphopoietin (TSLP) or TSLP receptor antibody is used in or with the drug delivery device of the present disclosure. In some embodiments, the drug delivery device may contain or be used with Avsola™ (infliximab-axxq), anti-TNF a monoclonal antibody, biosimilar to Remicade® (infliximab) (Janssen Biotech, Inc.) or another product containing infliximab for the treatment of autoimmune diseases. In some embodiments, the drug delivery device may contain or be used with Kyprolis® (carfilzomib), (2S)—N—((S)-1-((S)-4-methyl-1-((R)-2-methyloxiran-2-yl)-1-oxopentan-2-ylcarbamoyl)-2-phenylethyl)-2-((S)-2-(2-morpholinoacetamido)-4-phenylbutanamido)-4-methylpentanamide, or another product containing carfilzomib for the treatment of multiple myeloma. In some embodiments, the drug delivery device may contain or be used with Otezla® (apremilast), N-[2-[(1S)-1-(3-ethoxy-4-methoxyphenyl)-2-(methylsulfonyl) ethyl]-2,3-dihydro-1,3-dioxo-1H-isoindol-4-yl]acetamide, or another product containing apremilast for the treatment of various inflammatory diseases. In some embodiments, the drug delivery device may contain or be used with Parsabiv™ (etelcalcetide HCl, KAI-4169) or another product containing etelcalcetide HCl for the treatment of secondary hyperparathyroidism (sHPT) such as in patients with chronic kidney disease (KD) on hemodialysis. In some embodiments, the drug delivery device may contain or be used with ABP 798 (rituximab), a biosimilar candidate to Rituxan®/MabThera™, or another product containing an anti-CD20 monoclonal antibody. In some embodiments, the drug delivery device may contain or be used with a VEGF antagonist such as a non-antibody VEGF antagonist and/or a VEGF-Trap such as aflibercept (Ig domain 2 from VEGFR1 and Ig domain 3 from VEGFR2, fused to Fc domain of IgG1). In some embodiments, the drug delivery device may contain or be used with ABP 959 (eculizumab), a biosimilar candidate to Soliris®, or another product containing a monoclonal antibody that specifically binds to the complement protein C5. In some embodiments, the drug delivery device may contain or be used with Rozibafusp alfa (formerly AMG 570) is a novel bispecific antibody-peptide conjugate that simultaneously blocks ICOSL and BAFF activity. In some embodiments, the drug delivery device may contain or be used with Omecamtiv mecarbil, a small molecule selective cardiac myosin activator, or myotrope, which directly targets the contractile mechanisms of the heart, or another product containing a small molecule selective cardiac myosin activator. In some embodiments, the drug delivery device may contain or be used with Sotorasib (formerly known as AMG 510), a $KRAS^{G12c}$ small molecule inhibitor, or another product containing a $KRASG^{12}c$ small molecule inhibitor. In some embodiments, the drug delivery device may contain or be used with Tezepelumab, a human monoclonal antibody that inhibits the action of thymic stromal lymphopoietin (TSLP), or another product containing a human monoclonal antibody that inhibits the action of TSLP. In some embodiments, the drug delivery device may contain or be used with AMG 714, a human monoclonal antibody that binds to Interleukin-15 (IL-15) or another product containing a human monoclonal antibody that binds to Interleukin-15 (IL-15). In some embodiments, the drug delivery device may contain or be used with AMG 890, a small interfering RNA (siRNA) that lowers lipoprotein(a), also known as Lp(a), or another product containing a small interfering RNA (siRNA) that lowers lipoprotein(a). In some embodiments, the drug delivery device may contain or be used with ABP 654 (human IgG1 kappa antibody), a biosimilar candidate to Stelara®, or another product that contains human IgG1 kappa antibody and/or binds to the p40 subunit of human cytokines interleukin (IL)-12 and IL-23. In some embodiments, the drug delivery device may contain or be used with Amjevita™ or Amgevita™ (formerly ABP 501) (mab anti-TNF human IgG1), a biosimilar candidate to Humira®, or another product that contains human mab anti-TNF human IgG1. In some embodiments, the drug delivery device may contain or be used with AMG 160, or another product that contains a half-life extended (HLE) anti-prostate-specific membrane antigen (PSMA)×anti-CD3 BiTE® (bispecific T cell engager) construct. In some embodiments, the drug delivery device may contain or be used with AMG 119, or another product containing a delta-like ligand 3 (DLL3) CART (chimeric antigen receptor T cell) cellular therapy. In some embodiments, the drug delivery device may contain or be used with AMG 119, or another product containing a delta-like ligand 3 (DLL3) CART (chimeric antigen receptor T cell) cellular therapy. In some embodiments, the drug delivery device may contain or be used with AMG 133, or another product containing a gastric inhibitory polypeptide receptor (GIPR) antagonist and GLP-1R agonist. In some embodiments, the drug delivery device may contain or be used with AMG 171 or another product containing a Growth Differential Factor 15 (GDF15) analog. In some embodiments, the drug delivery device may contain or be used with AMG 176 or another product containing a small molecule inhibitor of myeloid cell leukemia 1 (MCL-1). In some embodiments, the drug delivery device may contain or be used with AMG 199 or another product containing a half-life extended (HLE) bispecific T cell engager construct (BITE®). In some embodiments, the drug delivery device may contain or be used with AMG 256 or another product containing an anti-PD-1×IL21 mutein and/or an IL-21 receptor agonist designed to selectively turn on the Interleukin 21 (IL-21) pathway in programmed cell death-1 (PD-1) positive cells. In some embodiments, the drug delivery device may contain or be used with AMG 330 or another product containing an anti-CD33×anti-CD3 BiTE® (bispecific T cell engager) construct. In some embodiments, the drug delivery device may contain or be used with AMG 404 or another product containing a human anti-programmed cell death-1(PD-1) monoclonal antibody being investigated as a treatment for patients with solid tumors. In some embodiments, the drug delivery device may contain or be used with AMG 427 or another product containing a half-life extended (HLE) anti-fms-like tyrosine kinase 3 (FLT3)×anti-CD3 BiTE® (bispecific T cell engager) construct. In some embodiments, the drug delivery device may contain or be used with AMG 430 or another product containing an anti-Jagged-1 monoclonal antibody. In some embodiments, the drug delivery device may contain or be used with AMG 506 or another product containing a multi-specific FAP×4-1BB-targeting DARPin® biologic under investigation as a treatment for solid tumors. In some embodiments, the drug delivery device may contain or be used with AMG 509 or another product containing a bivalent T-cell engager and is designed using XmAb® 2+1 technology. In some embodiments, the drug delivery device may contain or be used with AMG 562 or another product containing a half-life extended (HLE) CD19×CD3 BiTE® (bispecific T cell engager) construct. In some embodiments, the drug delivery device may contain or be used with Efavaleukin alfa (formerly AMG 592) or another product containing an IL-2 mutein Fc fusion protein. In some embodiments, the drug delivery device may contain or be used with AMG 596 or another product containing a CD3× epidermal growth factor receptor vIII (EGFRvIII) BiTE® (bispecific T cell engager) molecule. In some embodiments, the drug delivery device may contain or be used with AMG 673 or another product containing a half-life extended (HLE) anti-CD33×anti-CD3 BiTE® (bispecific T cell engager) construct. In some embodiments, the drug delivery device may contain or be used with AMG 701 or another product containing a half-life extended (HLE) anti-B-cell maturation antigen (BCMA)×anti-CD3 BiTE® (bispecific T cell engager) construct. In some embodiments, the drug delivery device may contain or be used with AMG 757 or another product containing a half-life extended (HLE) anti-delta-like ligand 3 (DLL3)×anti-CD3 BiTE® (bispecific T cell engager) construct. In some embodiments, the drug delivery device may contain or be used with AMG 910 or another product containing a half-life extended (HLE) epithelial cell tight junction protein claudin 18.2×CD3 BiTE® (bispecific T cell engager) construct.

Although the drug delivery devices, assemblies, components, subsystems and methods have been described in terms of exemplary embodiments, they are not limited thereto. The detailed description is to be construed as exemplary only and does not describe every possible embodiment of the present disclosure. Numerous alternative embodiments could be implemented, using either current technology or technology developed after the filing date of this patent that would still fall within the scope of the claims defining the invention(s) disclosed herein.

Those skilled in the art will recognize that a wide variety of modifications, alterations, and combinations can be made with respect to the above described embodiments without departing from the spirit and scope of the invention(s) disclosed herein, and that such modifications, alterations, and combinations are to be viewed as being within the ambit of the inventive concept(s).

What is claimed is:
1. A gas-driven drug delivery device comprising:
   a drug container having a drug outlet and configured to contain a drug;
   a plunger slidably coupled with the drug container;
   a gas chamber configured to contain a pressurized gas; and
   a piston assembly including:
      a flexible pushrod workingly coupled with the plunger,
      a non-linear guide including a non-linear guide pathway at least partially surrounding the flexible pushrod,
      a cylinder having a gas inlet and a bore at least partially surrounding the flexible pushrod, the gas inlet configured to be at least selectively in fluid communication with the gas chamber, and a piston in operable communication with the flexible pushrod and movable within the bore of the cylinder in response to the pressurized gas entering the cylinder through the gas inlet.

2. The gas-driven drug delivery device of claim 1, wherein the drug container has a longitudinal axis between the drug outlet and the plunger, and wherein the bore of the cylinder is one of parallel to the longitudinal axis of the drug container or perpendicular to the longitudinal axis of the drug container.

3. The gas-driven drug delivery device of claim 1 wherein the bore of the cylinder has a bore diameter, the flexible pushrod has a pushrod diameter, and the bore diameter is greater than the pushrod diameter.

4. The gas-driven drug delivery device of claim 1, wherein the gas-driven piston assembly further includes a pushrod support between the piston and the flexible pushrod.

5. The gas-driven drug delivery device of claim 1, wherein the flexible pushrod is made from at least one of pre-tensioned stainless steel extension spring stock, wire rope, and polymer tubing.

6. The gas-driven drug delivery device of claim 1, wherein the non-linear guide pathway has a uniform curvature or a variable curvature.

7. The gas-driven drug delivery device of claim 1, wherein the non-linear guide pathway has an interior surface including a low-friction material.

8. The gas-driven drug delivery device of claim 1, wherein the non-linear guide has a pushrod inlet, and at least one of (a) a chamfered edge on the pushrod inlet, or (b) a bushing at the pushrod outlet.

9. The gas-driven drug delivery device of claim 1 further comprising a plunger coupling in operable communication with the plunger, wherein the plunger coupling has at least one of:
   (a) a plunger connection projection that is received within a recess in a proximal face of a plunger,
   (b) a foot in operable communication with the plunger and configured to distribute an output force from the flexible pushrod across a proximal face of the plunger, and/or
   (c) a pushrod connection projection connected to an interior of the flexible pushrod.

\* \* \* \* \*